United States Patent [19]

Hemphill et al.

[11] Patent Number: 4,837,152

[45] Date of Patent: * Jun. 6, 1989

[54] PROCESS FOR REGENERATING SOYBEANS

[75] Inventors: John K. Hemphill, Cupertino; Claire A. Warshaw, Palo Alto, both of Calif.

[73] Assignee: Sungene Technologies Corporation, Palo Alto, Calif.

[*] Notice: The portion of the term of this patent subsequent to Aug. 4, 2004 has been disclaimed.

[21] Appl. No.: 890,302

[22] Filed: Jul. 29, 1986

[51] Int. Cl.$^4$ .............................................. C12N 5/00
[52] U.S. Cl. .......................... 435/240.49; 435/240.5; 435/240.54
[58] Field of Search ............ 435/240.5, 240.49, 240.54

[56] References Cited

U.S. PATENT DOCUMENTS 4,003,156 1/1977 Sibi et al.
4,684,612 8/1987 Hemphill et al. ................ 435/240.5

OTHER PUBLICATIONS

Hu et al., 1983, p. 213, In: Handbook of Plant Cell Culture, vol. 1, Evans et al., eds., Macmillan: New York.
Stuart et al., 1984, Plant Sci. Lett. 34:165–174.
Tilton et al., 1984, J. Plant Physiol. 115:191–200.
Phillips et al., *Plant Cell Tissue Organ Culture* 1, 123 (1981).
Widholm et al., *Plant Cell Reports* 2, 19 (1983).
Gamborg et al., *Plant Cell Reports* 2, 209 (1983a).
Gamborg et al., *Plant Cell Reports* 2, 213 (1983b).
Christianson et al., *Science* 222, 632 (1983).
Ranch et al., *In Vitro Cell Develop. Biol.* 21, 653 (1985).
Barwale et al., *Planta* 167, 473 (1986).
Kerns et al., *Plant Cell Reports* 5, 140 (1986).
Lazzeri et al., *Plant Molec. Biol. Rptr.* 3, 160 (1985).
Li et al., *Plant Cell Reports* 4, 344 (1985).
Grant, *Plant Cell, Tissue and Organ Culture* 3, 169 (1984).
Wright et al., *Plant Cell Reports* 5, 150 (1986).
Cheng et al., *Plant Science Letters* 19, 91 (1980).
Saka et al., *Plant Science Letters* 19, 193 (1980).
Kameya et al., *Plant Science Letters* 21, 289 (1981).
Ghazi, T. D. et al., *Plant Cell Reports* 5, 452 (1986).

*Primary Examiner*—Charles F. Warren
*Assistant Examiner*—David T. Fox
*Attorney, Agent, or Firm*—Robbins & Laramie

[57] ABSTRACT

The present invention relates to the regeneration of soybeans. The process comprises the steps of inducing callus and embryoid formation from tissue of a soybean plant, maturing the embryoids, germinating the embryoids, and forming roots on the germinated embryoids.

32 Claims, No Drawings

PROCESS FOR REGENERATING SOYBEANS

CROSS REFERENCE TO RELATED APPLICATION

The present invention is related to copending application Ser. No. 635,222, filed July 27, 1984, U.S. Pat. No. 4,684,612, incorporated by reference herein.

BACKGROUND OF THE INVENTION

1. Field of the Invention

The present invention relates to an improved process for regenerating soybeans (Glycine max (L.) Merrill). More particularly, the invention relates to the use of tissue and cell culture for the regeneration of soybean plantlets for many soybean varieties. The invention also relates to the media used in this process.

2. Description of the Prior Art

Plant regeneration from cells in culture is essential for the application of somatic hybridization, for the production of new varieties through somoclonal variation and for the use of genetic engineering in producing new varieties. Although plants can be regenerated from single cells of a large number of crop species, the efforts with soybean have generally been unsuccessful.

In recent years, plant cell culture successes have had a considerable influence on the understanding of the respective roles of cell and organism in control of plant growth and development. Isolated plant cells have been shown to be amenable to in vitro culture and complete plants could be regenerated from cultures derived from somatic cells, either directly via somatic embryogenesis or indirectly via organogenesis. Generally the regeneration pathway of choice is determined empirically by the manipulation of extrinsic factors, especially growth regulators. Early investigations of certain plant species have suggested that exogenous auxin concentration is the major factor controlling somatic embryogenesis, such that its reduction leads to the initiation of embryoid formation. In other species, exposure to a definite balance of auxin and cytokinin leads to the formation of organogenesis (shoots, then roots).

Phillips et al., in *Plant Cell Tissue Organ Culture* 1, 123 (1981), described the somatic embryogenesis of soybean in cell suspension or on agar. They utilized hypocotyl or epicotyl tissue for callus initiation on L2 medium. Cell suspension cultures were initiated from callus tissue in S2 medium. The cell suspension culture could be used to produce globular and heart-shaped embryos or additional callus which could form shoot buds. The formation of somatic embryos or shoot buds was reproducible using basal S2 or L2 media supplemented with 100 mg/l casein hydrolysate, 2.25 $\mu$M 2,4-dichlorophenoxyacetic acid (2,4-D), 0.1 $\mu$M abscisic acid (ABA), 0.1 $\mu$M 2-isopropyl-4-dimethylamino5-methylphenyl-1-piperidine carboxymethyl chloride (AMO 1618) and either 15 $\mu$M adenine or 0.46 $\mu$M kinetin. Although somatic embryos or shoot buds were formed, on plants were obtained for any varieties of *Glycine max*.

Wildholm et al., in *Plant Cell Reports* 2, 19 (1983), describe the formation of shoots from *Glycine canescens* callus obtained from hypocotyls or cotyledons. Root formation did not occur, so no plantlets were obtained. The method did not produce shoots when *Glycine max* (soybean) was the source of the tissue. The formation of shoots from *Glycine canescens* tissue culture was achieved through callus induction on B5 basal medium containing 0.5 mg/l $\alpha$-naphthalene acetic acid (NAA) followed in series by MS basal medium containing 0.5 mg/l of indoleacetic acid (IAA) and 5 mg/l benzyladenine (BA), and finally MS basal medium containing 0.5 mg/l BA.

Gamborg et al., in *Plant Cell Reports* 2, 209 (1983a), disclose somatic embryogenesis from cell suspension culture in several *Glycine* species including three cultivars (out of seven tested) of *Glycine max*. The embryoid induction medium utilized consisted of the major salts of SL, the micronutrients and vitamins of B5, 10 mg/l casamino acids, 15 $\mu$M adenine sulfate, 0.2 $\mu$M picloram and 0.025-0.25 $\mu$M AMO 1618. It was discovered that picloram was necessary for embryo induction and that it could be replaced by 0.5 to 2.0 $\mu$M 2,4-D. No embryoids were induced when the auxins NAA, IAA or indole-3-butyric acid (IBA) were utilized in place of the auxins picloram or 2,4-D. After embryoids were induced, they were transferred to embryo growth medium which consisted of SL medium containing various combinations of cytokinins (zeatin or BA), auxins (picloram) and gibberellic acid (GA$_3$). Embryoids which were formed went to a heart-shaped structure, but failed to develop beyond this stage on the induction medium. Transfer to the growth medium did result in the formation of roots, but shoots were not formed. The use of MS medium or addition of abscisic acid, coconut milk or change in osmolarity did not result in further development.

Gamborg et al., in *Plant Cell Reports* 2, 213 (1983b), describe the preparation of protoplasts from cell cultures of *Glycine tabacina* and *Glycine soja* and from leaf tissue from the soybean *Glycine max* cultivar (cv.) Williams 82. The protoplasts formed cells which could be induced to form heart-shaped embryos by the procedure of Gamborg et al (1983). As in the latter reference, no plantlets were formed from the procedure.

Christianson et al, in *Science* 222, 632 (1983a), disclose the regeneration of a plantlet from cell suspension culture of the soybean *Glycine max* (L.) Merrill cv. Mitchell. This appears to have been the result of a random even and appears to have resulted from a piece of clonal tissue. Immature embryos were aseptically removed from 2.5-3.0 cm pods, and embryo axes were cut into 1-2 mm pieces. These pieces were placed on a solid medium to induce callus formation. This medium consisted of MS salts, 0.5 mg/l nicotinic acid, 0.5 mg/l pyridozine, 100 mg/l thiamine, 100 mg/l inositol, 2% sucrose and 5 mg/l 2,4-D. The hard, non-friable tissue was selected for transfer to new medium and resulted in a tissue line that gave rise to hard, green, glossy, abnormal embryos. When the callus tissue was transferred from the induction medium to a N-amended medium and then transferred back to the induction medium, one exceptional piece of tissue was obtained which was covered with small embryoids. The N-amended medium consisted of the induction medium in which the two nitrogen salts of the MS salts were replaced with 20 mM ammonium citrate. Transfer of the embryoids to a medium containing 0.005 mg/l IBA and 0.2 mg/l BA gave rise to shoot formation. Transfer of the shoots to a basal medium containing 0.1 mg/l of IAA resulted in root formation to produce plantlets. This procedure does not appear to be generally applicable for regenerating soybean cultivars, but instead appears to have been a random event which may not be reproducible. Support for this analysis lies in Christianson et al.'s source of the embryogenic tissue. Christianson et al. state that "one exceptional piece of tissue" with embryoids was obtained. Since only one was obtained out of many initiated, it implies that this regeneration was a random even and could have been clonal in nature.

Copending application Ser. No. 356,222 discloses a method for regenerating several cultivars of soybean (*Glycine max*). In the process described in that application, an immature embryo is cultured in the light on a first medium which contains either 2,4-D, a mixture of 2,4-D and IAA, or a mixture of 2,4-D, IAA and ABA as the hormone to induce callus formation and embryoid formation from the callus. The embryoids are matured by culturing them on a second medium which is selected from a group of five media. The mature embryoids are then cultured on a third medium to induce shoot formation. The hormone utilized in the third medium may be a mixture of IBA and BA, a mixture of IAA and adenine sulfate, a mixture of IBA, BA and $GA_3$, or a mixture of IAA, BA and $GA_3$. Shoots are transferred to a fourth medium which is either hormone-free or contains the hormone IAA or IBA to induce the formation of roots.

Ranch, J. P., et al., *In Vitro Cell Develop. Boil.* 21, 653 (1985) discloses a method for regenerating several cultivars of soybean. In this process, callus tissue is initiated and somatic embryos formed by culturing immature embryos in the light (50 lux) on a first medium which contains 2,4-D. The somatic embryos are matured in the dark by culturing on a medium which contains IBA or a mixture of IBA and ABA as the hormone. The maturation medium is either liquid or solid. The embryos are germinated by culturing in the light (100 lux) on a medium containing a mixture of IBA and $GA_3$ as the hormone. The young plants are transferred to medium containing IBA for root development and cultured in the light (1500 lux).

Soybean plants and seeds are produced by this process. The resulting soybean plants may differ from the starting plant material as a result of somoclonal variation. The pathway is also useful in that it will enable the use of various selection processes to provide further variation. Plants which are produced can be used in conventional breeding programs.

SUMMARY OF THE INVENTION

The process of the present invention comprises the steps of inducing callus and embryoid formation from tissue of a soybean plant, maturing the embryoids, germinating the embryoids, and forming roots on the germinated embryoids.

More specifically, in one embodiment, the present process comprises the steps of:

(a) inducing callus and embryoid formation from tissue of a soybean plant by culturing on a first medium comprising mineral salts, vitamins, sucrose, 2,4-D, and optionally ABA and/or amino acids;

(b) maturing the embryoids by subculturing on a second medium comprising mineral salts, vitamins, sucrose and a hormone selected from the group consisting of a mixture of IAA and t-zeatin and a mixture of IAA, t-zeatin, ABA and picloram;

(c) germinating the embryoids by subculturing the embryoids on a third medium comprising mineral salts, vitamins, sucrose, a hormone selected from the group consisting of a mixture of IAA, kinetin, ABA and $GA_3$ and a mixture of BA and IBA and optionally amino acids; and (d) rooting the germinated embryoids by subculturing on a fourth medium comprising mineral salts, vitamins, sucrose and optionally a hormone selected from the group consisting of IAA and IBA.

In a second embodiment, the process comprises the steps of:

(a) inducing pre-callus formation from tissue of a soybean plant by culturing on a first medium comprising mineral salts, vitamins, 2,4-D and optionally amino acids;

(b) completing the formation of callus, and forming embryoids and partially maturing the embryoids by subculturing on a second medium comprising mineral salts, vitamins, sucrose, a mixture of 2,4-D, ABA and IAA and optionally amino acids;

(c) further maturing the embryoids by subculturing on a liquid third medium comprising mineral salts, vitamins, sucrose, amino acids and a mixture of 2,4-D and ABA;

(d) germinating the embryoids by subculturing on a fourth medium comprising mineral salts, vitamins, sucrose and a hormone selected from the group consisting of a mixture of NAA, BA, t-zeatin and kinetin, a mixture of IAA, kinetin, ABA and $GA_3$ and a mixture of BA and IBA; and (e) rooting the germinated embryoids by subculturing on a fifth medium comprising mineral salts, vitamins, sucrose and optionally a hormone selected from the group consisting of IBA and IAA.

The soybean donor tissue may also be cultured on a preconditioning medium prior to culturing on the first medium in the second embodiment. The pre-conditioning medium comprises mineral salts, vitamins, sucrose and 2,4-D.

The source of the tissue is preferably immature embryos from cultivars of *Glycine max* (L.) Merrill. Suitable cultivars include Williams 82, Corsoy 79, Forrest, Mitchell 450, Beeson 80, Miami, Century 84, Evans, Gnome, and Northrup King variety 5-18-84-8032-23.

DETAILED DESCRIPTION OF THE INVENTION

The present invention is directed to an improved process for regenerating soybeans (*Glycine max*) through the use of cell or tissue culture. In this process, regenerated soybean plantlets are obtained which can be placed in soil and grown to maturation. The present invention is also directed to soybean plants obtained by this process and seeds obtained from these plants.

In general, the process comprises (a) inducing callus and embryoid formation from donor tissue of a soybean plant, (b) maturing the embryoids, (c) germinating the mature embryoids, and (d) forming roots on the germinated embryoids which results in the formation of a plant or plantlet. Optionally, in one embodiment, the soybean donor tissue can be first pre-conditioned before being placed into this process. Each of the media utilized in this process contain mineral salts, vitamins and sucrose. In addition, each medium contains a different scheme of hormones to accomplish the desired result, i.e., plant regeneration.

The plant donor tissue which is preferred for use in the initiation of callus and embryoid formation is the immature embryo. The immature embryos are isolated from pods which are periodically harvested from the soybean plant. Pods are usually harvested when they reach the size of 1.5–2.5 cm in length. The pods are surface-sterilized and the embryos are removed aseptically. The embryos are 0.5–7 mm in length. It is preferred to use embryos that are 1–4 mm in length. If the embryos are smaller than 1 mm, they must be matured before being plated onto the first medium. Embryos can be matured as described in copending application Ser. No. 635,222.

At least two embodiments can be utilized to regenerate soybeans in accordance with the present invention. The first embodiment is slower than the second, especially through the steps of callus induction, embryoid formation and embryoid maturation. Each embodiment will be described separately.

In the first step of the first embodiment, the immature embryo is cultured to induce callus and embryoid formation. This is accomplished by culturing the immature embryos on a first medium A.

The first medium A comprises mineral salts, vitamins and sucrose. The mineral salts comprise macroelements and microelements. The macroelements used in the first medium may be the following compounds: magnesium sulfate, calcium chloride, monopotassium phosphate, potassium nitrate and ammonium nitrate. The microelements contained in the first medium A are: boric acid, manganese sulfate, zinc sulfate, sodium molybdate (VI), copper (II) sulfate, cobalt chloride, potassium, iodide, iron (II) sulfate and disodium EDTA.

The preferred amounts of the macroelements and microelements used to prepare one liter of the first medium A are as follows: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 16.9 mg manganese sulfate monohydrate, 8.6 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 41.7 mg iron (II) sulfate heptahydrate, and 55.9 mg disodium EDTA. This combination of mineral salts is known in the art as the MS mineral salts, which has been modified so that the medium contains more iron and EDTA, one and one-half times more than the standard MS mineral salts.

The first medium A also contains vitamins. The vitamins used include nicotinic acid, glycine, pyridoxine, thiamine, folic acid and biotin. These vitamins are known in the art as Nitsch's vitamins. The Nitsch's vitamins have been modified so that they contain more thiamine, and optionally less nicotinic acid. In addition to these vitamins, the first medium also contains myoinositol. The amount of myoinositol utilized may be 100 mg/l, 1,500 mg/l or 1,600 mg/l.

The preferred amounts of vitamins used to prepare one liter of the first medium A are as follows: 5 mg nicotinic acid, 2 mg glycine, 0.5 mg pyridoxine hydrochloride, 0.9 mg thiamine hydrochloride, 0.5 mg folic acid and 0.05 mg biotin. This vitamin mixture will be referred to herein as modified Nitsch's vitamins A, and is preferred in the first medium. It is also possible to utilize modified Nitsch's vitamins B. This vitamin mixture is identical except that 10.4 mg/l thiamine hydrochloride and 0.5 mg/l nicotinic acid are used. A third vitamin mixture may also be used, which will be referred to herein as modified Nitsch's vitamins C. This vitamin mixture is identical to modified Nitsch's vitamins A, except that 10.4 mg/l thiamine hydrochloride is used.

The first medium A contains 2%–3% sucrose, preferably 2%, and a gelling substance such as agar or Gelrite (trademark, Kelco Commercial Development). It is preferred to use Gelrite at a concentration of 0.2%. The medium has a pH of 5.5–6.0 with a preferred pH of 5.8.

In addition to the above components, the first medium A also contains 2,4-D as the hormone. 2,4-D is generally present in the first medium A at a concentration of about 5 mg/l to about 10 mg/l. It is preferred to use 5 mg/l 2,4-D in the first medium A. Optionally, first medium A also contains ABA at a concentration of about 0.0264 mg/l. The first medium may also optionally contain amino acids selected from the group consisting of L-glutamine at a concentration of 2.19 g/l and a mixture of 800 mg/l L-glutamine, 350 mg/l L-methionine and 200 mg/l L-asparagine. This latter combination will be referred to herein as amino acids. A. The first medium A is sterilized by autoclaving all of the components except the vitamins, amino acids, ABA and 2,4-D which are sterilized by microporous membrane filtration.

It is preferred to culture to immature embryo on the first medium for about 25 to about 35 days before transferring to the second medium. Culturing on the first medium is conducted in the light, such as a Grow-Lux fluorescent light or a cool white fluorescent light, with a photoperiod of 16 hours, at a temperature of 25°–29° C.

After culturing the immature embryo on the first medium, the callus with embryoids is subcultured on a second medium to mature the embryoid. The callus with the embryoids is subcultured on the second medium in the light for 20–45 days, preferably for about 25–35 days per subculture, to mature the embryoids. It may be necessary to transfer the maturing embryoids to fresh medium during this time period in order to obtain complete maturation. The maturing embryoids are transferred based on their morphological appearance, i.e., their similarity to natural zygotic embryos. Any second medium may be utilized for the transfer.

The second medium may be selected from a group consisting of three different media. Each second medium contains 2% to 3%, preferably 2%, sucrose and a gelling substance, preferably Gelrite. In addition to these components, the second medium may also contain 1,000–4,000 mg/l mannitol. The pH is 5.5–6.0, preferably 5.8. Each medium is sterilized by autoclaving except the vitamins and hormones, which are filter-sterilized.

Second medium A comprises mineral salts, vitamins, casein hydrolysate and a hormone. The mineral salts are the same as in the first medium, except that 4.524 g of ammonium citrate and 1.010 g of $KNO_3$ are utilized in place of 1.65 g of ammonium nitrate and 1.9 g of $KNO_3$. This composition will be referred to as mineral salts A. The vitamins are the same as in the first medium, preferably modified Nitsch's vitamins A. 100 mg/l of myoinositol is preferably used. Preferably 100 mg/l of casein hydrolysate is utilized, as is 0.4% Gelrite. The hormone which is utilized is a mixture of IAA, t-zeatin, ABA and picloram. It is preferred to use about 1.0 mg/l IAA, about 1.0 mg/l t-zeatin, about 0.0264 mg/l ABA, and about 0.0096 mg/l picloram.

Second medium B comprises the same mineral salts and vitamins as in the first medium. It is preferred to use modified Nitsch's vitamins A. 100 mg/l of myoinositol is preferably used. The hormone which is utilized in second medium B is a mixture of IAA and t-zeatin, preferably at a concentration of about 1 mg/l IAA and 0.5 mg/l t-zeatin.

Second medium C comprises mineral salts, vitamins, casein hydrolysate and a hormone. The mineral salts are the same as in the first medium, except that 4.524 g/l of ammonium citrate is used in place of ammonium nitrate and $KNO_3$. This composition of mineral salts will be referred to as mineral salts B. Myoinositol is preferably present at 100 mg/l, and 100 mg/l of casein hydrolysate is used. 0.4 mg/l Gelrite is used in this medium. The vitamins are the same as in the first medium, preferably modified Nitsch's vitamins A. The hormone which is utilized is the same as in second medium A.

In this embodiment, the most preferred second medium is second medium C, with second medium B being the next preferred medium.

After maturing the embryoids, the third step is to germinate the embryoids by transferring and subculturing them on a germinating medium, hereinafter referred to as the third medium. The embryoids are subcultured on the third medium in the light for 20–45 days, preferably for about 25–35 days per subculture. It may be necessary to transfer the material to fresh medium during this time period. If transfers are made, they may be done after 20–45 days, preferably after 30 days. Transferring is usually done if the shoots have not elongated properly. That is, if the shoots do not have two sets of leaves, they are transferred to fresh third medium or onto a modified third medium containing one-half the concentration of the macroelements other than iron or one-half the concentration of all of the mineral salts except for iron, with the other components being the same, before they are placed on the fourth medium. It is preferred to use one or more subcultures on modified third medium B, as described further below, if additional transfers are necessary.

The third medium which can be utilized to germinate the embryoids may be selected from a group consisting of two different media, hereinafter referred to as third medium A or B. Each third medium contains 2%–3%, preferably 2%, sucrose and a gelling substance, preferably 0.2% Gelrite. The pH is 5.5–6.0, preferably 5.8. Each medium is sterilized by autoclaving, except that the vitamins, hormones and amino acids are sterilized by membrane filtration.

Third medium A comprises mineral salts, vitamins, amino acids and a hormone. The mineral salts are the same as used in the first medium, except that 2 g of $NH_4NO_3$ and 600 mg of $KNO_3$ are used. This combination of mineral salts will be referred to as mineral salts C. The vitamins which are used include thiamine hydrochloride and pyridoxine hydrochloride. THe vitamins are known in the art as Sussex's vitamins. Sussex's vitamins are present at 15 mg/l thiamine hydrochloride and 1.5 mg/l pyridoxine hydrochloride. Myoinositol is preferably present at 1,500 mg/l concentration. The amino acids which are used include L-glutamine, L-serine and L-asparagine. The mixture of these vitamins is known in the art as Sussex's amino acids. Preferred amounts of these amino acids are 500 mg/l L-glutamine, 100 mg/l L-serine and 100 mg/l L-asparagine. The hormone which is utilized is a mixture of IAA, kinetin, ABA and $GA_3$. It is preferred to use about 0.01 mg/l IAA, 0.1 mg/l kinetin, 0.1 mg/l ABA and 0.1 mg/l $GA_3$.

Third medium B comprises mineral salts, vitamins and a hormone. The mineral salts and vitamins are the same as used in the first medium. Preferably, modified Nitsch's vitamins A is utilized, as is 100 mg/l myoinositol. The hormone which may be utilized is a mixture of BA and IBA, preferably at a concentration of 0.2 mg/l, BA, and 0.005 mg/l IBA. In addition, a mineral salt composition which has the same concentration of microelements and iron as the first medium, but only one-half the concentration of the macroelements, can be used in this medium. Such a combination will be referred to herein as mineral salts D. Alternatively, a mineral salt composition which has one-half the concentration of all of the mineral salts, except iron, can be used. Such a combination will be referred to herein as mineral salts E. These compositions with lower mineral salt concentrations will be referred to herein as modified third medium B.

After germinating the embryoids, the fourth step is to root the germinated embryoids by transferring to a root-forming medium, hereinafter referred to as the fourth medium. The shoots are subcultured on the fourth medium in the light for 20–60 days, preferably for about 30 days. Due to slow root development, it may be necessary to transfer the material to fresh medium during this time period. The transfer can be to fresh fourth medium or to a modified fourth medium A or C in which all the macroelements, except iron, are present at one-half the concentration in the original fourth medium. Alternatively, a mineral salt composition having one-half the concentration of all of the mineral salts except iron and EDTA can be used in modified fourth medium A or C.

The fourth medium which is used to root the germinated embryoids may be selected from a group consisting of three media A–C. Each medium contains 1%–2%, preferably 1%, sucrose and a gelling substance, preferably 0.2% Gelrite. The pH is 5.5–6.0, preferably 5.8. Each medium is sterilized by autoclaving except the vitamins and hormones which are sterilized by membrane filtration.

Fourth medium A comprises mineral salts and vitamins which are the same as in the first medium. It is preferred to use modified Nitsch's vitamins A. Preferably, 100 mg/l myoinositol is utilized. No hormone is present in this medium. It is also possible to utilize mineral salts D or mineral salts E in this medium.

Fourth medium B comprises mineral salts, vitamins and a hormone. The mineral salts are the same as in the first medium, except that 300 mg/l $NH_4H_2PO_4$ and 2.5 g $KNO_3$ are used in place of the $NH_4NO_3$ and $KNO_3$. This combination will be referred to herein as mineral salts F. Likewise, the vitamins are the same with modified Nitsch's vitamins A preferred. 100 mg/l myoinositol and 1% sucrose are present. The hormone is IAA with a preferred concentration of 0.5 mg/l.

Fourth medium C comprises mineral salts, vitamins and a hormone. The mineral salts and vitamins are the same as in fourth medium A, including the use of mineral salts D or E. The hormone is either IAA or IBA, at a concentration of 0.1–0.5 mg/l. Myoinositol is present at 100 mg/l.

After the roots have formed, the plantlets are ready to be potted in soil. The plantlets are potted by transferring the plantlets to soil which is well moistened and contained in a high humidity chamber. Once the plantlets are established, they are removed from the high humidity chamber, transplanted to soil, and grown to maturity to produce seeds.

In the second embodiment, the first step comprises the culturing of the immature embryo on a first medium B to induce pre-callus formation. Alternatively, the immature embryo is first cultured on a pre-conditioning medium before culturing on the first medium B. The pre-conditioning medium is the same as the first medium A, except that the concentration of 2,4-D is about 1 mg/l to about 2 mg/l. Modified Nitsch's vitamins A is preferably utilized. The immature embryo is cultured on a pre-conditioning medium in the dark at room temperature for about 10 to about 21 days, preferably 14 days, before transferring to first medium B.

First medium B comprises mineral salts, vitamins, sucrose, 2,4-D and optionally amino acids. The mineral salts are the same as described for first medium A. The vitamins are also the same as for first medium A, i.e., modified Nitsch's vitamins A, modified Nitsch's vitamins B or modified Nitsch's vitamins C. Modified Nitsch's vitamins A is preferred. Myoinositol is used at a concentration of 100 mg/l or 1,600 mg/l. 2%–3%, preferably 2%, sucrose and a gelling substance, preferably 0.2% Gelrite, are present. The hormone is 2,4-D, preferably at 10 mg/l concentration. The first medium may optionally contain amino acids, such as L-glutamine or a mixture of L-glutamine, L-methionine and L-asparagine. This latter mixture will be referred to hereinafter as amino acids A. Preferably 800 mg/l L-glutamine or a mixture of 800 mg/l L-glutamine, 350 mg/l L-methionine and 200 mg/l L-asparagine is used. The medium has a pH of 5.5–6.0, preferably 5.8. The medium is sterilized by autoclaving all of the components except the vitamins, 2,4-D and amino acids, which are filter-sterilized. The immature embryo is cultured on this medium for about 7–14 days, preferably 7 days, before transferring to a second medium D. The culturing is conducted in the light, such as either Grow-Lux fluorescent light or cool white fluorescent light, with a photoperiod of 16 hours per day. The pre-callused immature embryo is cultured on second medium D to complete callus formation, form embryoids, and to partially mature the embryoids. Culturing on the second medium D is performed in the light as previously described for about 14–35 days, preferably for 21 days.

Second medium D comprises mineral salts, vitamins, a hormone, and optionally amino acids. The mineral salts are the same as used in the first medium B. The vitamins are also the same, but are preferably modified Nitsch's vitamins B. Myoinositol may be used at a concentration of 100 mg/l or 1,600 mg/l. The hormone is a mixture of 2,4-D, IAA and ABA, preferably at a concentration of about 3 mg/l 2,4-D, 2 mg/l IAA and 0.0264 mg/l ABA. The amino acids which may optionally be present are the same as in the first medium B.

The next step is to further mature the embryoids by culturing in a liquid medium, hereinafter referred to as third medium C. Culturing in this medium is conducted in the light as previously described for about 7–14 days, preferably 7 days, with shaking. It is preferred to utilize baffled flasks for proper aeration and to perform gentle shaking on a vertical shaker with slow rotation, preferably 5–10 rpm.

Third medium C comprises mineral salts, vitamins, amino acids and a hormone. The mineral salts are the same as in the first medium B. The vitamins are also the same, but preferably modified Nitsch's vitamins B. The amino acids may either be L-glutamine at 500–800 mg/l, amino acids A or a mixture of L-alanine, L-arginine and L-serine at concentrations of 250 mg/l, 250 mg/l and 100 mg/l, respectively. This mixture will be referred to as amino acids B. The medium may optionally contain coconut milk at 0.5% concentration. The hormone is a mixture of 2,4-D and ABA at a concentration of 0.5 mg/l 2,4-D and 0.0264 mg/l ABA. Myoinositol is present at 100 mg/l or 1,600 mg/l, and sucrose at 2%. The pH is 5.5–6.0, preferably 5.8. It is preferred to use third medium C without coconut milk and with L-glutamine as the amino acid. The third medium C may also contain 1,000–4,000 mg/l mannitol.

After maturing the embryoids in the third medium C, the embryoids are germinated by culturing on a fourth medium. The culturing of the embryoids for germination is generally performed as described above for the first embodiment. It is preferred to first use fourth medium D as the germinating medium with one or more subcultures on this medium. The germinated embryoids will be transferred as discussed in the first embodiment, generally to modified third medium B. The recalcitrant embryoids will preferably be subcultured on fourth medium E in the light for 7–14 days, and then back to fourth medium D and cultured as previously described.

The fourth medium which may be utilized for germinating the embryoids is selected from a group consisting of four different media, herein referred to as fourth media D–G as discussed above. Each fourth medium contains 2%–3%, preferably 2%, sucrose and a gelling substance, preferable 0.2% Gelrite. The pH is 5.5–6.0, preferably 5.8. Each medium is sterilized by autoclaving, except the vitamins, hormones and amino acids, which are filter-sterilized.

Fourth medium D comprises mineral salts, vitamins and a hormone. The mineral salts and vitamins are the same as for first medium B, with modified Nitsch's vitamins B preferred. In addition, mineral salts D or one-half concentration of all mineral salts may also be utilized. Myoinositol is present at 100 mg/l or 1,600 mg/l, and sucrose at 2%. The hormone is a mixture of NAA, BA, t-zeatin and kinetin. The concentrations of each are preferably 0.05–0.15mg/l NAA. about 0.033 mg/l BA, about 0.033 mg/l t-zeatin, and about 0.033 mg/l kinetin. It is preferred to use 0.15 mg/l NAA. This combination of hormones is known in the art as Collins' germinating hormones.

Fourth medium E is the same as fourth medium D, except for the hormone concentrations. It is preferred to use about 0.05 mg/ml NAA, about 0.33 mg/l BA, about 0.33 mg/l t-zeatin and about 0.33 mg/l kinetin in fourth medium E. This combination of hormones is also known as Collins' germinating hormones.

Fourth medium F and fourth medium G are the same as third medium A and third medium B described above for the first embodiment.

Following germination, the shoots are rooted by culturing on a fifth medium. THe culturing of the shoots is performed as described above for the first embodiment. The fifth medium may be selected from a group of three media, hereinafter referred to as fifth media A-C. Fifth media A, B and C are the same as fourth media A, B and C, respectively, for the first embodiment. Plants are transferred to the soil as previously described.

This process is useful for regenerating plantlets from tissue of many cultivars of soybean. The process is useful for regenerating plantlets from *Glycine max* (L.) Merrill cv. Williams 82, Beeson 80, Miami, Century 84, Forrest, Corsoy 79, Mitchell 450, Evans, Gnome and Northrup King variety S-18-84-8032023. All cultivars are available commercially or by contacting Dr. Richard L. Bernard, University of Illinois Department of Agronomy, Urbana, Ill. 61801 (Northern cultivars) or by contacting Dr. E. E. Hartwig, U.S. Department of Agriculture, Agricultural Research Center, Stoneville, Mo. 38776 (Southern cultivars).

The present invention will be further described by reference to the following non-limiting examples. In these examples, culturing in the light refers to culturing in light having a photoperiod of 16 hours per day at 25°–29° C. unless indicated otherwise. The temperature during the 8 hour dark phase is 23°–24° C. unless indicated otherwise. In all of the media, any one of the three modified Nitsch's vitamins could be used.

EXAMPLE 1

Preparation of Solutions

The following stock solutions were prepared for use in making the media described in further detail below.

1. Mineral Salts

A. MS Minor Salts

A 100X stock solution of the MS minor salts was prepared by dissolving the following components in 500 ml of distilled, deionized water.

| Component | Weight (mg) | Component | Weight (mg) |
|---|---|---|---|
| $ZnSO_4.7H_2O$ | 430 | KI | 41.5 |
| $Na_2MoO_4.2H_2O$ | 12.5 | $H_3BO_3$ | 310 |
| $CuSO_4.5H_2O$ | 1.25 | $MnSO_4.H_2O$ | 845 |
| $CoCl_2.6H_2O$ | 1.25 | | |

B. Mineral Salts A

A 10X stock solution of mineral salts A was prepared by dissolving the following components in 500 ml of distilled, deionized water.

| Component | Weight (mg) | Component | Weight (mg) |
|---|---|---|---|
| $NH_4$ Citrate | 22,620 | $MnSO_4.H_2O$ | 84.5 |
| $KNO_3$ | 5,050 | $ZnSO_4.7H_2O$ | 43 |
| $CaCl_2.2H_2O$ | 2,200 | $Na_2MoO_4.2H_2O$ | 1.25 |
| $MgSO_4.2H_2O$ | 1,850 | $CuSO_4.5H_2O$ | 0.125 |
| $KH_2PO_4$ | 850 | KI | 4.15 |
| $H_3BO_3$ | 31 | $CoSO_4.7H_2O$ | 0.125 |
| $FeSO_4.7H_2O$ | 279.5 | $Na_2$ EDTA | 208.5 |

C. Mineral Salts B

A 10X stock solution of mineral salts B was prepared by dissolving the following components in 500 ml of distilled, deionized water.

| Component | Weight (mg) | Component | Weight (mg) |
|---|---|---|---|
| $NH_4$ Citrate | 22,620 | $ZnSO_4.H_2O$ | 43 |
| $CaCl_2.2H_2O$ | 2,200 | $Na_2MoO_4.2H_2O$ | 1.25 |
| $MgSO_4.7H_2O$ | 1.850 | $CuSO_4.5H_2O$ | 0.125 |
| $KH_2PO_4$ | 850 | KI | 4.15 |
| $H_3BO_3$ | 31 | $CoSO_4.7H_2O$ | 0.125 |
| $MnSO_4.7H_2O$ | 84.5 | $Na_2$ EDTA | 208.5 |
| $FeSO_4.7H_2O$ | 279.5 | | |

D. Mineral Salts C

A 10X stock solution of mineral salts C was prepared by dissolving the following components in 500 ml of distilled, deionized water.

| Component | Weight (mg) | Component | Weight (mg) |
|---|---|---|---|
| $NH_4NO_3$ | 10,000 | $MnSO_4.H_2O$ | 84.5 |
| $KNO_3$ | 3,000 | $ZnSO_4.7H_2O$ | 43 |
| $CaCl_2.2H_2O$ | 2,200 | $Na_2MoO_4.2H_2O$ | 1.25 |
| $MgSO_4.2H_2O$ | 1,850 | $CuSO_4.5H_2O$ | 0.125 |
| $KH_2PO_4$ | 850 | KI | 4.15 |
| $H_3BO_3$ | 31 | $CoSO_4.7H_2O$ | 0.125 |
| $FeSO_4.7H_2O$ | 279.5 | $Na_2$ EDTA | 208.5 |

E. Mineral Salts F

A 10X stock solution of mineral salts F was prepared by dissolving the following components in 500 ml of distilled, deionized water.

| Component | Weight (mg) | Component | Weight (mg) |
|---|---|---|---|
| $NH_4H_2PO_4$ | 1,500 | $MnSO_4.H_2O$ | 84.5 |
| $KNO_3$ | 12,500 | $ZnSO_4.7H_2O$ | 43 |
| $CaCl_2.2H_2O$ | 2,200 | $Na_2MoO_4.2H_2O$ | 1.25 |
| $MgSO_4.2H_2O$ | 1,850 | $CuSO_4.5H_2O$ | 0.125 |
| $KH_2PO_4$ | 850 | KI | 4.15 |
| $H_3BO_3$ | 31 | $CoSO_4.7H_2O$ | 0.125 |
| $FeSO_4.7H_2O$ | 279.5 | $Na_2$ EDTA | 208.5 |

2. Vitamins

A. Nitsch's Vitamins A

A 100X stock solution of vitamins was prepared by dissolving the following components in distilled, deionized water of a total volume of 500 ml. The folic acid was first dissolved in 5 ml of 1N KOH before adding it to the water.

| Component | Weight (mg) | Component | Weight (mg) |
|---|---|---|---|
| nicotinic acid | 250 | thiamine.HCl | 25 |
| glycine | 100 | folic acid | 25 |
| pyridoxine.HCl | 25 | biotin | 2.5 |

B. Nitsch's Vitamins B

A 100X stock solution of vitamins was prepared by dissolving the following components in distilled, deionized water of a total volume of 500 ml. The folic acid was first dissolved in 5 ml of 1N KOH before adding it to the water.

| Component | Weight (mg) | Component | Weight (mg) |
|---|---|---|---|
| nicotinic acid | 25 | thiamine.HCl | 500 |
| glycine | 100 | folic acid | 25 |
| pyridoxine.HCl | 25 | biotin | 2.5 |

C. Nitsch's Vitamins C

A 100X stock solution of vitamins was prepared by dissolving the following components in distilled, deionized water of a total volume of 500 ml. The folic acid was first dissolved in 5 ml of 1N KOH before adding it to the water.

| Component | Weight (mg) | Component | Weight(mg) |
|---|---|---|---|
| nicotinic acid | 250 | thiamine.HCl | 500 |
| glycine | 100 | folic acid | 25 |
| pyridoxine.HCl | 25 | biotin | 2.5 |

D. Sussex's Vitamins

A 100X stock solution of Sussex's vitamins was prepared by dissolving 750 mg of thiamine hydrochloride and 75 mg of pyridoxine hydrochloride in 500 ml of distilled, deionized water.

3. Amino Acids

A. L-Glutamine

An 80 mg/ml stock solution was prepared by dissolving 20 g of L-glutamine in 250 ml of distilled, deionized water.

B. Amino Acids A

A stock solution of amino acids A was prepared by dissolving 20 g of L-glutamine, 8.75 g of l-methionine and 5 g of L-asparagine in 250 ml of distilled, deionized water.

C. Sussex's Amino Acids

A stock solution of Sussex's amino acids was prepared by dissolving 20 g of L-glutamine, 2.5 g of serine and 2.5 g of L-asparagine in 250 ml of distilled, deionized water.

D. Amino Acids B

A stock solution of amino acids B was prepared by dissolving 6.25 g of L-alanine, 6.25 g of L-arginine and 2.5 g of L-serine in 250 ml of distilled, deionized water.

4. Iron and EDTA

A 100X stock solution of iron and EDTA was prepared by dissolving 1.39 g of iron (II) sulfate heptahydrate and 1.86 g of disodium-EDTA in 500 ml of distilled, deionized water.

5. Hormones (A) A 0.264 mg/ml stock solution of ABA was prepared by dissolving 26.4 mg of ABA in 20 ml of 1M $NaHCO_3$ and diluting to 100 ml with distilled, deionized water.

(B) A 1 mg/l stock solution of BA was prepared by dissolving 100 mg of BA in 20 ml of 1N NaOH and diluting to 100 ml with distilled, deionized water.

(C) A 1 mg/ml stock solution of 2,4-D was prepared by dissolving 100 mg of 2,4-D in 20 ml of 70% ethanol and diluting to 100 ml with distilled, deionized water.

(D) A 1 mg/ml stock solution of IBA was prepared by dissolving 100 mg of IBA in 20 ml of 70% ethanol and diluting to 100 ml with distilled, deionized water.

9E) A 1 mg/ml stock solution of kinetin was prepared by dissolving 100 mg of kinetin in 20 ml of 1N NaOH and diluting to 100 ml with distilled, deionized water.

(F) A 1 mg/ml stock solution of t-zeatin was prepared by dissolving 100 mg of t-zeatin in 5 ml of 5N HCl and diluting to 100 ml with distilled, deionized water.

(G) A 0.0025 mg/ml stock solution of picloram was prepared by dissolving 0.24 mg of picloram in 20 ml of warm, distilled, deionized water and diluting to 100 ml with distilled, deionized water.

(H) A 0.1 mg/ml stock solution of IAA was prepared by dissolving 10 mg of IAA in 20 ml of 70% ethanol and diluting to 100 ml with distilled, deionized water. The stock solution was stored in a bottle wrapped in aluminum foil in a refrigerator. The solution was prepared fresh every one to two months.

(I) A 1 mM stock solution of $GA_3$ was prepared by dissolving 34.6 mg of $GA_3$ in 20 ml of absolute ethanol and diluting to 100 ml with distilled, deionized water.

EXAMPLE 2

Preparation of Media

1. First Medium A

The first medium A was prepared by dissolving one packet of Murashige minimal organics solution without sucrose (Gibco Laboratories Catalog No. 510–3118), which contained 100 mg myoinositol and 0.4 mg thiamine hydrochloride, 20 g of sucrose and 2 g of Gelrite in 800 ml of distilled, deionized water. 5 ml of the iron and EDTA stock solution were then added. The mixture was brought to the desired volume with distilled, deionized water, depending on the amount of vitamins and hormone stock solutions to be added after autoclaving. The final volume when all components were added was one liter. The pH was adjusted to 5.8 with 1 N HCl or 1 N NaOH. The mixture was autoclaved at 18 psi for 15 minutes.

10 ml of either modified Nitsch's vitamins A stock solution, modified Nitsch's vitamins B stock solution, or modified Nitsch's vitamins C stock solution were filter-sterilized by passing through a 0.22 micron Millipore membrane filter and added to the cooling medium. The appropriate volume of the 2,4-D stock solution, and optionally the appropriate volume of ABA, was added after filter-sterilization to give the desired concentration, i.e., 5–19 mg/l 2.4-D, and optionally 0.0264 mg/l ABA, to the cooling medium. If amino acids were desired, either 2.19 g/l of L-glutamine were added to the 800 ml of water, or 10 ml of filter-sterilized amino acids A stock solution was added to the cooling medium. The medium was then poured into petri dishes.

2. First Medium B

First medium B was prepared as described above for first medium A, using 10 mg/l 2,4-D. If first medium B contained 1,600 mg/l myoinositol, an additional 1.5 g of myoinositol were also dissolved in the 800 ml of water.

3. Pre-Conditioning Medium

Pre-conditioning medium was prepared as described for the first medium, having a concentration of 1.2 mg/l 2,4-D. The medium was poured into petri dishes.

4. Second Medium

A. Second Medium A

Second medium A was prepared by dissolving 20 g of sucrose and 4 g of Gelrite, 100 mg of casein hydrolysate, and either 100 mg or 1.5 g of myoinositol in 800 ml of distilled, deionized water. 100 ml of mineral salts A stock solution were added, and the mixture brought to the desired volume as described above. The pH was adjusted to 5.8, and the mixture autoclaved as previously described. 10 ml of either modified Nitsch's vitamins A stock solution, modified Nitsch's vitamins B stock solution or modified Nitsch's vitamins C stock solution were filter-sterilized and added to the cooling medium. The appropriate volumes of the hormone stock solutions were filter-sterilized and added to the cooling medium to give the desired concentration, i.e., 1 mg/l IAA, 1 mg/l t-zeatin, 0.0264 mg/l ABA, and 0.0096 mg/l picloram. The medium was poured into petri dishes.

B. Second Medium B

Second medium B was prepared as described for first medium A, except that the appropriate amounts of the IAA and t-zeatin stock solutions were used in place of 2,4-D to give the desired concentration, i.e., 1 mg/l IAA and 0.5 mg/l t-zeatin. In addition, 1.5 g of myoinositol were also dissolved in the water, if desired.

C. Second Medium C

Second medium C was prepared as described for second medium A, except that mineral salts B stock solution was used and 100 mg of myoinositol were dissolved in the water.

D. Second Medium D

Second medium D was prepared as described for first medium B, except that the appropriate amounts of the 2,4-D, IAA and ABA stock solutions were used in place of 2,4-D only to give the desired concentrations, i.e, 3 mg/l 2,4-D, 2 mg/l IAA, and 0.0264 mg/l ABA. Modified Nitsch's vitamins B was preferred.

5. Third Medium (Fourth Medium)

A. Third Medium A (Fourth Medium F)

Third medium A was prepared by dissolving 20 g of sucrose, w g of Gelrite, and either 1.5 g or 100 mg of myoinositol in 800 ml of distilled, deionized water. 100 ml of mineral salts C stock solution was added, and the volume brought to the desired level as described above. The pH was adjusted to 5.8 and autoclaved as described above. 10 ml of Sussex's vitamins stock solution, 10 ml of Sussex's amino acids stock solution and the appropriate volumes of the IAA, kinetin, ABA and $GA_3$ stock solutions to give the desired concentrations, i.e., 0.01 mg/l IAA, 0.1 mg/l kinetin, 0.1 mg/l ABA and 0.1 mg/l $GA_3$, were filter-sterilized and added to the cooling medium, which was then poured into petri dishes.

B. Third Medium B (Fourth Medium G)

Third medium B was prepared as described for first medium A, except that the appropriate amounts of the BA and IBA stock solutions were used in place of 2,4-D to give the desired concentrations, i.e., 0.2 mg/l BA and 0.005 mg/l IBA. The medium was poured into petri dishes.

Modified third medium B, having one-half the concentration of macroelements except iron, was prepared as described for first medium A except that only one-half packet of Murashige medium was dissolved. 50 mg of myoinositol and 0.2 mg of thiamine hydrochloride were also dissolved in the water. 10 ml of the iron and EDTA stock solution and 5 ml of the MS minor salts stock solution were also added.

Modified third medium B, having one-half the concentration of all mineral salts except iron was prepared as described above except that the MS minor salts stock solution was not added.

C. Third Medium C

Third medium C was prepared as described for first medium B, except that no Gelrite was used, either 6.25–10 ml of the L-glutamine stock solution, 10 ml of amino acids A stock solution or 10 ml of the amino acids B stock solution were used, and the appropriate amounts of 2,4-D and ABA were used to give the desired concentrations, i.e., 0.5 mg/l 2,4-D and 0.0264 mg/l ABA. Modified Nitsch's vitamins B was preferred. If coconut milk was present, it was added to a final concentration of 0.5%. The medium was poured into buffered flasks.

6. Fourth Medium

A. Fourth Medium A (Fifth Medium A)

Fourth medium A was prepared as described for first medium A, except that only 10 g of sucrose were used and 2,4-D was excluded. The medium was poured into petri dishes. Fourth medium A, having one-half the concentration of macroelements except iron, or of all mineral salts except iron, was prepared analogously to that described for third medium B.

B. Fourth Medium B (fifth Medium B)

Fourth medium B was prepared as described for second medium A, except that 10 g of sucrose, 2 g of Gelrite, 100 ml of mineral salts F stock solution and the appropriate amount of IAA to give the desired concentration, i.e., 0.5 mg/l, were used. The medium was poured into petri dishes.

C. Fourth Medium C (Fifth Medium C)

Fourth medium C, including one-half strength macroelements except iron, or all mineral salts except iron and EDTA, was prepared as described for fourth medium A except that the appropriate amounts of either the IAA or the IBA stock solution were added to give the desired concentration, i.e., 0.1–0.5 mg/l.

D. Fourth Medium D

Fourth medium D was prepared as described for first medium B, except that the appropriate amounts of NAA, BA, t-zeatin and kinetin stock solutions were used to give the desired concentrations, i.e., 0.05–0.15 mg/l NAA, 0.033 mg/l BA, 0.033 mg/l t-zeatin and 0.033 mg/l kinetin. Modified Nitsch's vitamins B was preferred. Modified fourth medium D, having one-half the concentration of macroelements except iron and EDTA or of all mineral salts except iron and EDTA, was prepared analogously to that previously described.

E. Fourth Medium E

Fourth medium E or modified fourth medium E was prepared as described for fourth medium D, except that the desired concentrations of hormones were 0.05 mg/l NAA, 0.33 mg/l BA, 0.33 mg/l t-zeatin and 0.33 mg/l kinetin.

EXAMPLE 3

Soybean Regeneration

Immature embryos were isolated from pods of the soybean *Glycine max* (L.) Merrill cv. Corsoy 79 or Mitchell 450, when the pods were 1.5 to 5.0 cm in length. The soybean pods were collected each morning and placed in a sterile 18 oz. bottle. Surface-sterilizing agents employed separately were as follows: 70% ethanol (1 min.), 15% concentrated Clorox TM and 0.1% Tween 80 (8 min.), and washing three times with distilled, deionized water. Sterile pods were placed in the top of a sterile petri dish (100 mm×25 mm). Each pod was individually cut with scissors. The ovules (two to three per pod) were carefully pressed out of the pod into the bottom petri dish (sterile). A pair of forceps and a needle probe were used to remove the immature embryo from each ovule. The embryos were plated onto the first medium A contained in a petri dish. First medium A contained 10 mg/l 2,4-D, 0.0264 mg/l ABA, 2.19 g/l L-glutamine and modified Nitsch's vitamins A. The petri dish was placed in the light (cool white) and cultured for 28 days to form calli and embryoids.

At this time, each callus with embryoids was transferred to second medium C and cultured on this medium for 28 days in the light (cool white). The callus with mature embryoids was then transferred to a third medium B and cultured on this medium for 28 days in the light (cool white). The germinating embryos were transferred to modified third medium B containing one-half concentration of all mineral salts except iron and EDTA and cultured for 28 days in the light (cool white). The germinating embryos were again transferred to this medium and cultured an additional 28 days. The germinated embryoids were then transferred to fourth medium B. The shoots were cultured on this medium for 28 days in the light (cool white). During this time, the shoots formed roots.

The Gelrite was washed off the roots of the plantlets with sterile, distilled, deionized water. The plantlets were then transferred to soil in a quart Mason jar. The bottom of the Mason jar was covered with sterile, activated charcoal. Four inches of an autoclaved, equal mixture of vermiculite, Perlite and potting soil were placed over the charcoal The plantlets were planted in the soil and the soil was well moistened with sterile, distilled, deionized water. Parafilm TM was placed over the jar and the cap was screwed over the Parafilm. The jar was then placed in a Percival growth chamber at 24° C., having a photoperiod of 16 hours per day. After 12 days, the jar was removed from the growth chamber and placed in a sweater box in the greenhouse. A second sweater box was placed perpendicular to and over the first sweater box and a paper towel was placed over it to provide for diffuse sunlight. The greenhouse maintained a temperature of 29° C.±3° C. during the day and 21° C.±2° C. during the night, and a photoperiod of 16 hours per day. After one week, the Parafilm was removed from the jar. Four days later, the regenerated plants were transplanted to a 6" pot containing an equal mixture of vermiculite, perlite and potting soil, and returned to the sweater boxes. The regenerated plant flowered and formed pods which contained developing ovules.

EXAMPLE 4

Soybean Regeneration

Soybean plants were regenerated from immature embryos as described in Example 3, except that second medium A was used in place of second medium C.

EXAMPLE 5

Immature embryos were isolated from the Corsoy 79 cultivar as described in Example 3, plated on first medium A containing 5 mg/l 2,4-D, and cultured in the light (cool white). After 28 days, the callus with embryoids was transferred to second medium A and cultured for 30 days in the light (cool white). The callus with mature embryoids was then transferred to third medium B and cultured in the light (cool white). The germinating embryos are cultured and transferred as described in Example 3 to produce plants, except that only the macroelements, except iron and EDTA, are at one-half concentration in modified third medium B.

EXAMPLE 6

Soybean plants are regenerated as described in Example 5, except that second medium C was used in place of second medium A, and culturing on this medium was for 24 days.

EXAMPLE 7

Soybean plants are regenerated as described in Example 6, except that third medium A was used in place of third medium B, and culturing on second medium B was for 28 days.

EXAMPLE 8

Soybean plants are regenerated as described in Example 7, except that second medium B was used in place of second medium C.

EXAMPLE 9

Immature embryos were isolated from the Williams 82 cultivar as described in Example 3, plated on first medium A containing 5 mg/l 2,4-D, and cultured in the light (cool white). After 18 days, the callus with embryoids was transferred to second medium A and cultured for 41 days in the light (cool white). The callus with mature embryoids was then transferred to third medium A and cultured in the light. The germinating embryos are cultured and transferred as described in Example 3 to produce plants, except that only the macroelements, except iron and EDTA, are at one-half concentration in modified third medium B.

EXAMPLE 10

Soybean plants are regenerated as described in Example 9, except that the embryos were cultured on first medium A for 28 days, second medium C and third medium B were utilized, and the callus with embryoids was cultured on second medium C for 31 days.

EXAMPLE 11

Soybean plants are regenerated as described in Example 10, except that second medium B was used in place of second medium C.

EXAMPLE 12

Immature embryos were isolated from the Corsoy 79 cultivar as described in Example 3, plated on first medium B containing 10 mg/l 2,4-D, and cultured in the light (Grow-Lux). After 8 days, the pre-callus was transferred to second medium D and cultured in the light (Grow-Lux) for 19 days. The callus was maturing embryoids was then placed in third medium C, which is a liquid and cultured in the light (Grow-Lux) with gentle shaking for 13 days. The callus with mature embryoids was then transferred to fourth medium D having 0.15 mg/l NAA and cultured in the light (Grow-Lux) for 29 days. The embryoids were transferred to fourth medium D having 0.15 mg/l NAA and cultured in the light (Grow-Lux). The germinating embryoids are cultured on and transferred from fourth medium D as described in example 3, i.e., to modified fourth medium G and then to fifth medium for germination and root formation, except that the light is grow-Lux and only the macroelements, except iron and EDTA, are at one-half concentration in modified fourth medium G. Embryoids which have not germinated on fourth medium D are cultured on fourth medium E for 70–14 days, and then returned to fourth medium D and cultured as above.

EXAMPLE 13

Immature embryos were isolated from the Williams 82 cultivar as described in Example 3, plated on first medium B containing 10 mg/l 2,4-D, and cultured in the light (cool white). After 14 days, the pre-callus was transferred to second medium D and cultured in the light (cool white) for 14 days. The callus with maturing embryoids was then placed in third medium C, which is a liquid, and cultured in the light (cool white) for 13 days. The callus with mature embryoids was then transferred to fourth medium D having 0.15 mg/l NAA and cultured in the light (cool white) for 29 days. The embryoids were transferred to fourth medium D having 0.15 mg/l NAA and cultured in the light (Grow-Lux). The germinating embryoids are cultured on and transferred from fourth medium D as described in Example 3, i.e., to modified fourth medium G and then to fifth medium for germination and root formation, except that only the macroelements, except iron and EDTA, are at one-half concentration in modified fourth medium G. Embryoids, which have not germinated on fourth medium D are cultured on fourth medium E for 7–14 days, and then returned to fourth medium D and cultured as above.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for regenerating soybean plants via somatic embryogenesis which comprises:
   (a) culturing a soybean embryo on a solid first medium which comprises MS mineral salts modified to contain 41.7 mg/l iron sulfate heptahydrate (ISH) and 55.9 mg/l disodium ethylenediamine tetracetic acid ($Na_2EDTA$), vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol and 5–10 mg/l 2,4-dichlorophenoxyacetic acid (2,4-D) in the light for 25–45 days to induce callus and embryoid formation;
   (b) subculturing the callus and embryoids on one or more solid second media which are selected from the group consisting of:
      (i) second medium A, which comprises MS mineral salts modified to contain no ammonium nitrate, 4,524 mg/l ammonium citrate, 1,010 mg/l potassium nitrate, 41.7 mg/l ISH and 55.9 mg/l $Na_2EDTA$, vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, 100 mg/l casein hydrolysate, myoinositol, 1 mg/l indoleacetic acid (IAA), 1 mg/l t-zeatin, 0.0264 mg/l abscisic acid (ABA) and 0.0096 mg/l picloram;
      (ii) second medium B, which comprises MS mineral salts modified to contain 41.7 mg/l ISH and 55.9 mg/l $Na_2$ EDTA, vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol, 1 mg/l IAA and 0.5 mg/l t-zeatin; and
      (iii) second medium C, which comprises MS mineral salts modified to contain no ammonium nitrate, no potassium nitrate, 4,524 mg/l ammonium citrate, 41.7 mg/l ISH, and 55.9 mg/l $Na_2EDTA$, vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, 100 mg/l casein hydrolysate, myoinositol, 1 mg/l IAA, 1 mg/l t-zeatin, 0.0264 mg/l ABA and 0.0096 mg/l picloram
   in the light for 20–45 days per subculture, to mature the embryoids;
   (c) subculturing the mature embryoids on one or more solid third media which are selected from the group consisting of:
      (i) third medium A, which comprises MS mineral salts modified to contain 2,000 mg/l ammonium nitrate, 600 mg/l potassium nitrate, 41.7 mg/l of ISH and 55.9 mg/l $Na_2EDTA$, Sussex's vitamins, Sussex's amino acids, 2%–3% sucrose, myoinositol, 0.01 mg/l IAA, 0.1 mg/l kinetin, 0.1 mg/l ABA and 0.1 mg/l gibberellic acid ($GA_3$); and
      (ii) third medium B, which comprises MS mineral salts modified to contain 41.7 mg/l ISH and 55.9 mg/l $Na_2EDTA$, vitamins selected from the group consisting of Nitsch's vitamins modified to contain 10.4 mg/l thiamine hydrochloride, and 0.5 mg/l nicotinic acid and Nitsch's vitamins modified to contain 10.4 mg/l of thiamine hydrochloride, 2%–3% sucrose, myoinositol, 0.2 mg/l benzyl adenine (BA) and 0.005 mg/l indole-3-butyric acid (IBA)
   in the light for 20–45 days for subculture, to induce shoot formation; and
   (d) subculturing the shoots on one or more solid fourth media which are selected from the group consisting of:
      (i) fourth medium A, which comprises MS mineral salts modified to contain 41.7 mg/l ISH and 55.9 mg/l $Na_aEDTA$, vitamins selected from the group consisting of Nitsch's vitamins modified to contain 10.4 mg/l thiamine hydrochloride, and 0.5 mg/l nicotinic acid and Nitsch's vitamins modified to contain 10.4 mg/l of thiamine hydrochloride, 1%–2% sucrose and myoinositol;
      (ii) fourth medium B, which comprises MS mineral salts modified to contain no ammonium nitrate, 300 mg/l $NH_4H_2PO_4$, 2,500 mg/l potassium nitrate, 41.7 mg/l ISH and 55.9 mg/l $Na_2EDTA$, vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 1%–2% sucrose, myoinositol and 0.5 mg/l IAA, and;
      (iii) fourth medium C, which comprises MS mineral salts modified to contain 41.7 mg/l ISH and 55.9 mg/l $Na_2EDTA$, vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 1%–2% sucrose, myoinositol and a hormone selected from the group consisting of 0.1–0.5 mg/l IAA and 0.1–0.5 IBA
   in the light for 20–45 per subculture, to induce root formation whereby plants are obtained.

2. The process of claim 1 wherein the MS mineral salts of the third medium B, fourth medium A and fourth medium C are further modified to contain one-half the concentration of the macroelements.

3. The process of claim 1 wherein the MS mineral salts of the third medium B, fourth medium A and fourth medium C are further modified to contain one-half the concentration of all the mineral salts except iron and EDTA.

4. The process of claim 1 wherein the concentration of myoinositol in third medium A is 1,500 mg/l and in all other media is 100 mg/l.

5. The process of claim 2 wherein the concentration of myoinositol in third medium A is 1,500 mg/l and in all other media is 100 mg/l.

6. The process of claim 3 wherein the concentration of myoinositol in third medium A is 1,500 mg/l and in all other media is 100 mg/l.

7. The process of claim 1 wherein the vitamins in third medium A is Sussex's vitamins and the vitamins in all other media is Nitsch's vitamins modified to contain 10.4 mg/l thiamine hydrochloride and 0.5 mg/l nicotinic acid.

8. The process of claim 1 wherein the vitamins in third medium A is Sussex's vitamins and the vitamins in all other media is Nitsch's vitamins modified to contain 10.4 mg/l thiamine hydrochloride and 0.5 mg/l nicotinic acid.

9. The process of claim 3 wherein the vitamins in third medium A is Sussex's vitamins and the vitamins in all other media is Nitsch's vitamins modified to contain 10.4 mg/l thiamine hydrochloride and 0.5 mg/l nicotinic acid.

10. The process of claim 4 wherein the vitamins in third medium A is Sussex's vitamins and the vitamins in all other media is Nitsch's vitamins modified to contain 10.4 mg/l thiamine hydrochloride and 0.5 mg/l nicotinic acid.

11. The process of claim 5 wherein the vitamins in third medium A is Sussex's vitamins and the vitamins in all other media is Nitsch's vitamins modified to contain 10.4 mg/l thiamine hydrochloride and 0.5 mg/l nicotinic acid.

12. The process of claim 6 wherein the vitamins in third medium A is Sussex's vitamins and the vitamins in all other media is Nitsch's vitamins modified to contain 10.4 mg/ thiamine hydrochloride and 0.5 mg/l nicotinic acid.

13. A process for regenerating soybean plants via somatic embryogenesis which comprises:
(a) culturing a soybean embryo on a solid first medium which comprises MS mineral salts modified to contain 41.7 mg/l iron sulfate heptahydrate (ISH) and 55.9 mg/l disodium ethylenediamine tetracetic acid (Na$_2$EDTA), vitamins selected from the group consisting of Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol and about 10 mg/l 2,4-dichlorophenoxyacetic acid (2,4-D) in the light for about 7–14 days to induce pre-callus formation;
(b) subculturing the pre-callus on a solid second medium which comprises MS mineral salts modified to contain 41.7 ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol, 3 mg/l 2,4-D, 2 mg/l indoleacetic acid (IAA) and 0.0264 mg/l abscisic acid (ABA) in the light for about 14 to about 35 days, to complete callus formation and embryoid formation and partial embryoid maturation;
(c) subculturing the embryoids in a liquid third medium which comprises MS mineral salts modified to contain 41.7 mg/l ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, an amino acid selected from the group consisting of 500–800 mg/l L-glutamine, a mixture of 800 mg/l L-glutamine, 350 mg/l L-methionine and 200 mg/l L-asparagine and a mixture of 250 mg/l L-alanine, 250 mg/l L-arginine and 100 mg/l L-serine, 2%–3% sucrose, myoinositol, 0.5 mg/l 2,4-D and 0.0264 mg/l ABA in the light for about 7–14 days, to complete the maturation of the embryoids;
(d) subculturing the mature embryoids on a solid fourth medium selected from the group consisting of:
(i) fourth medium A, which comprises MS mineral salts modified to contain 41.7 mg/l ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol, 0.05–0.15 mg/l α-naphthaleneacetic acid (NAA), 0.033 mg/l benzyladenine (BA), 0.033 mg/l t-zeatin and 0.033 mg/l kinetin;
(ii) fourth medium B, which comprises MS mineral salts modified to contain 41.7 mg/l ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol, 0.05 mg/l NAA, 0.33 mg/l benzyladenine (BA), 0.33 mg/l t-zeatin and 0.33 mg/l kinetin;
(iii) fourth medium C, which comprises MS mineral salts modified to contain 2,000 mg/l ammonium nitrate, 600 mg/l potassium nitrate, 41.7 mg/l of ISH and 55.9 mg/l Na$_2$EDTA, Sussex's vitamins, Sussex's amino acids, 2%–3% sucrose, myoinositol, 0.01 mg/l IAA, 0.1 mg/l kinetin, 0.1 mg/l ABA and 0.1 mg/l gibberellic acid (GA$_3$); and
(iv) fourth medium D, which comprises MS mineral salts modified to contain 41.7 mg/l ISH and 55.9 mg/l Na$_2$EDTA, vitamins selected from the group consisting of Nitsch's vitamins modified to contain 09 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol, 0.2 mg/l BA and 0.005 mg/l indole-3-butyric acid (IBA)
in the light for about 20–45 days per subculture, to induce shoot formation; and
(e) subculturing the shoots on one or more solid fifth media which are selected from the group consisting of:

(i) fifth medium A, which comprises MS mineral salts modified to contain 41.7 mg/l ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 1%–2% sucrose and myoinositol;

(ii) fifth medium B, which comprises MS mineral salts modified to contain no ammonium nitrate, 300 mg/l NH$_4$H$_2$PO$_4$, 2,500 mg/l potassium nitrate, 41.7 mg/l ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 1%–2% sucrose, myoinositol and 0.5 mg/l IAA, and;

(iii) fifth medium C, which comprises MS mineral salts modified to contain 41.7 mg/l ISH and 55.9 mg/l Na$_2$EDTA, vitamins selected from the group consisting of Nitsch's vitamins modified to contain 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 1%–2% sucrose, myoinositol and a hormone selected from the group consisting of 0.1–0.5 mg/l IAA or 0.1–0.5 IBA in the light for 20–45 days per subculture, to induce root formation whereby plants are obtained.

14. The process of claim 13 wherein the MS mineral salts of the fourth medium A, fourth medium B, fourth medium D, fifth medium A and fifth medium C are further modified to contain one-half the concentration of the macroelements.

15. The process of claim 13 wherein the MS mineral salts of the fourth medium A, fourth medium B, fourth medium D, fifth medium A and fifth medium C are further modified to contain one-half the concentration of all of the mineral salts except iron and EDTA.

16. The process of claim 13 wherein the first medium and second medium further contain an amino acid selected from the group consisting of 800 mg/l L-glutamine or a mixture of 800 mg/l L-glutamine, 350 mg/l L-methionine and 200 mg/l L-asparagine.

17. The process of claim 14 wherein the first medium and second medium further contain an amino acid selected from the group consisting of 800 mg/l L-glutamine or a mixture of 800 mg/l L-glutamine, 350 mg/l L-methionine and 200 mg/l L-asparagine.

18. The process of claim 15 wherein the first medium and second medium further contain an amino acid selected from the group consisting of 800 mg/l L-glutamine or a mixture of 800 mg/l L-glutamine, 350 mg/l L-methionine and 200 mg/l L-asparagine.

19. The process of claim 13 wherein the immature embryo is pre-conditioned prior to culturing on the first medium by culturing in the dark for about 10–21 days on a solid pre-conditioning medium which comprises MS mineral salts modified to contain 41.7 mg/l ISH and 55.9 mg/l Na$_2$EDTA, vitamins selected from the group consisting of Nitsch's vitamins modified to containing 0.9 mg/l thiamine hydrochloride, Nitsch's vitamins modified to contain 10.4 mg/l thiamine hydrochloride and 0.5 mg/l nicotinic acid and Nitsch's vitamins modified to contain 10.4 mg/l of thiamine hydrochloride, 2%–3% sucrose, myoinositol and 1–2 mg/l 2,4-D.

20. The process of claim 13 wherein the concentration of myoinositol in fourth medium C is 1,500 mg/l and in all other media is 100 mg/l.

21. The process of claim 14 wherein the concentration of myoinositol in fourth medium C is 1,500 mg/l and in all other media is 100 mg/l.

22. The process of claim 15 wherein the concentration of myoinositol in fourth medium C is 1,500 mg/l and in all other media is 100 mg/l.

23. The process of claim 16 wherein the concentration of myoinositol in fourth medium C is 1,500 mg/l and in all other media is 100 mg/l.

24. The process of claim 17 wherein the concentration of myoinositol in fourth medium C is 1,500 mg/l and in all other media is 100 mg/l.

25. The process of claim 18 wherein the concentration of myoinositol in fourth medium C is 1,500 mg/l and in all other media is 100 mg/l.

26. The process of claim 19 wherein the concentration of myoinositol in fourth medium C is 1,500 mg/l and in all other media is 100 mg/l.

27. The process of claim 13 wherein the vitamins in fourth medium C is Sussex's vitamins and the vitamins in all other media are Nitsch's vitamins modified to contain 10.4 mg/l thiamine hydrochloride and 0.5 mg/l nicotinic acid.

28. The process of claim 14 wherein the vitamins in fourth medium C is Sussex's vitamins and the vitamins in all other media are Nitsch's vitamins modified to contain 10.4 mg/l thiamine hydrochloride and 0.5 mg/l nicotinic acid.

29. The process of claim 15 wherein the vitamins in fourth medium C is Sussex's vitamins and the vitamins in all other media are Nitsch's vitamins modified to contain 10.4 mg/l thiamine hydrochloride and 0.5 mg/l nicotinic acid.

30. The process of claim 16 wherein the vitamins in fourth medium C is Sussex's vitamins and the vitamins in all other media are Nitsch's vitamins modified to contain 10.4 mg/l thiamine hydrochloride and 0.5 mg/l nicotinic acid.

31. The process of claim 17 wherein the vitamins in fourth medium C is Sussex's vitamins and the vitamins in all other media are Nitsch's vitamins modified to contain 10.4 mg/l thiamine hydrochloride and 0.5 mg/l nicotinic acid.

32. The process of claim 18 wherein the vitamins in fourth medium C is Sussex's vitamins and the vitamins in all other media are Nitsch's vitamins modified to contain 10.4 mg/l thiamine hydrochloride and 0.5 mg/l nicotinic acid.

* * * * *

UNITED STATES PATENT AND TRADEMARK OFFICE
CERTIFICATE OF CORRECTION

PATENT NO. : 4,837,152
DATED : June 6, 1989
INVENTOR(S) : John K. HEMPHILL

It is certified that error appears in the above-identified patent and that said Letters Patent is hereby corrected as shown below:

Claim 8, column 21, line 12, change "1" to -- 2 --.

Signed and Sealed this

Fifteenth Day of October, 1991

Attest:

*Attesting Officer*

HARRY F. MANBECK, JR.

*Commissioner of Patents and Trademarks*